US012718510B2

(12) United States Patent
Qian et al.

(10) Patent No.: US 12,718,510 B2
(45) Date of Patent: Aug. 25, 2026

(54) VISUALIZATION OF DTI DATA MERGED WITH A THREE-DIMENSIONAL MEDICAL MODEL IN AN AUGMENTED REALITY ENVIRONMENT

(71) Applicant: Medivis, Inc., New York, NY (US)

(72) Inventors: Long Qian, Brooklyn, NY (US); Osamah Choudhry, New York, NY (US); Christopher Morley, New York, NY (US)

(73) Assignee: Medivis, Inc., New York, NY (US)

( * ) Notice: Subject to any disclaimer, the term of this patent is extended or adjusted under 35 U.S.C. 154(b) by 78 days.

(21) Appl. No.: 18/673,263

(22) Filed: May 23, 2024

(65) Prior Publication Data

US 2025/0265796 A1 Aug. 21, 2025

Related U.S. Application Data

(63) Continuation-in-part of application No. 18/583,328, filed on Feb. 21, 2024, now Pat. No. 12,290,326.

(51) Int. Cl.

| | |
|---|---|
| ***G06T 19/00*** | (2011.01) |
| ***A61B 34/10*** | (2016.01) |
| ***A61B 90/00*** | (2016.01) |
| ***G06T 19/20*** | (2011.01) |
| ***G06V 10/25*** | (2022.01) |
| ***G06V 10/94*** | (2022.01) |
| ***G06V 20/20*** | (2022.01) |

(52) U.S. Cl.

CPC .............. *G06T 19/20* (2013.01); *A61B 34/10* (2016.02); *A61B 90/37* (2016.02); *G06T 19/006* (2013.01); *G06V 10/25* (2022.01); *G06V 10/945* (2022.01); *G06V 20/20* (2022.01); *A61B 2034/105* (2016.02); *A61B 2090/365* (2016.02); *G06T 2210/41* (2013.01); *G06T 2219/2012* (2013.01); *G06V 2201/03* (2022.01)

(58) Field of Classification Search

None

See application file for complete search history.

(56) References Cited

U.S. PATENT DOCUMENTS

2009/0270678 A1* 10/2009 Scott ...................... A61B 1/043 600/109
2019/0290361 A1* 9/2019 Shalayev ............... A61B 34/10
2020/0004225 A1* 1/2020 Buller ....................... B22F 5/04
2021/0015583 A1* 1/2021 Avisar .................. G06F 3/1454
2024/0225472 A1* 7/2024 Moreau .................. G06T 7/136

* cited by examiner

*Primary Examiner* — Nicholas R Wilson

(74) *Attorney, Agent, or Firm* — Cognition IP, P.C.; Edward Steakley; Saleh Kaihani

(57) ABSTRACT

An example operation includes merging diffusion tensor image (DTI) data associated with a scan of a patient body with a three-dimensional medical model to create a merged three-dimensional image in a three-dimensional coordinate space, identifying fibers of selected portions of the merged three-dimensional image associated with a region of interest defined by a virtual area selection performed by a physical instrument, highlighting the fibers as a fiber bundle, and displaying the highlighted fiber bundle as a colorized subset of the merged three-dimensional image.

20 Claims, 10 Drawing Sheets

VISUALIZATION OF DTI DATA MERGED WITH A THREE-DIMENSIONAL MEDICAL MODEL IN AN AUGMENTED REALITY ENVIRONMENT

CROSS-REFERENCE TO RELATED APPLICATIONS

This application is a continuation-in-part of U.S. patent application Ser. No. 18/583,328, entitled "VIRTUAL INTERACTIONS WITH INSTRUMENTS IN AUGMENTED REALITY," filed on Feb. 21, 2024, the entirety of which is incorporated by reference.

FIELD OF INVENTION

Various embodiments relate generally to augmented reality and more specifically to merging imaging data to provide an augmented reality (AR) model.

SUMMARY

The appended claims may serve as a summary of this application.

BRIEF DESCRIPTION OF THE DRAWINGS

The present invention relates generally to AR visualization for identifying regions of interest of a medical patient for use by a medical professional.

The present disclosure will become better understood from the detailed description and the drawings, wherein.

DETAILED DESCRIPTION

It will be readily understood that the instant components, as generally described and illustrated in the figures herein, may be arranged and designed in a wide variety of different configurations. Thus, the following detailed description of the embodiments of at least one of a method, apparatus, computer readable storage medium and system, as represented in the attached figures, is not intended to limit the scope of the application as claimed but is merely representative of selected embodiments. Multiple embodiments depicted herein are not intended to limit the scope of the solution. The computer-readable storage medium may be a non-transitory computer readable media or a non-transitory computer readable storage medium.

The instant features, structures, or characteristics described in this specification may be combined in any suitable manner in one or more embodiments. For example, the usage of the phrases "example embodiments," "some embodiments," or other similar language, throughout this specification refers to the fact that a particular feature, structure, or characteristic described in connection with the embodiment may be included in at least one example. Thus, appearances of the phrases "example embodiments", "in some embodiments", "in other embodiments," or other similar language, throughout this specification can all refer to the same embodiment. Thus, these embodiments may work in conjunction with any of the other embodiments, may not be functionally separate, and the described features, structures, or characteristics may be combined in any suitable manner in one or more embodiments.

Example embodiments provide methods, systems, hardware components, non-transitory computer readable media, devices, and/or networks, which provide for visualizing tractography data to identify a region of interest (ROI) of a person/patient. The patient may be a candidate for a surgical procedure, such as brain surgery, open heart surgery, orthopedic surgery of a joint or bone, etc.

Figure 1A:
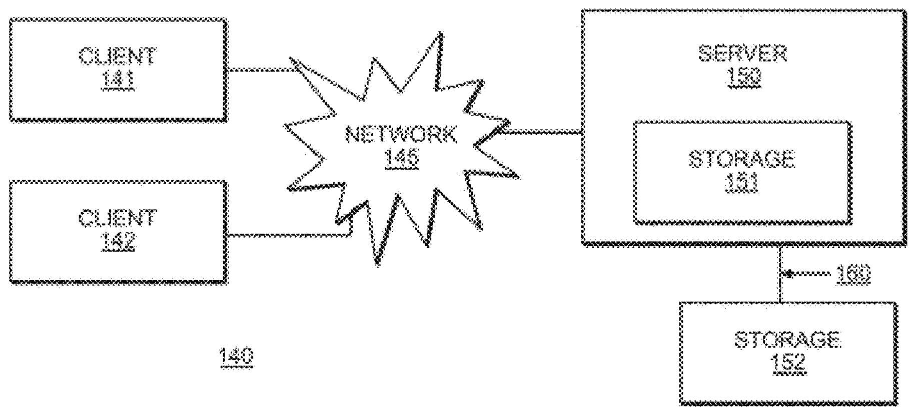
FIG. 1A illustrates an example network configuration according to example embodiments.

A diagram of an exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, a local area network (LAN), a wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
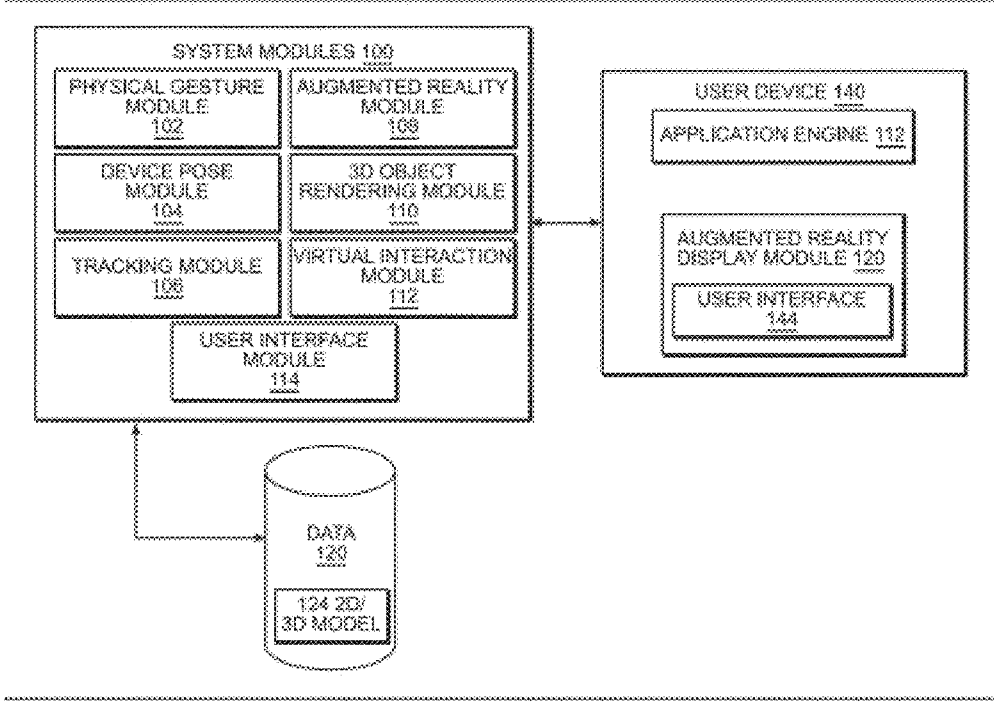
FIG. 1B is a block diagram illustrating an exemplary computer system that performs augmented reality (AR) processing according to example embodiments.

FIG. 1B illustrates a block diagram of an example system 100 that performs AR processing and which includes a physical gesture module 102, a device pose module 104, a tracking module 106, an AR module 108, a 3D object rendering module 110, a virtual interaction module 112 and a user interface module 114. The system 100 may communicate with a user device 140 to display output, via a user interface 144 generated by an application engine 142. In various embodiments, the user device 140 may be an AR display headset device that further includes one or more of the respective modules 102, 104, 106, 108, 110, 112, 114. The user device 140 may also be a display module that illustrates a live selection made by a hand-held instrument brought near an area of a patient and which may include a virtual tip or extension that appears to enter the body on the display but which is not actually touching the patient body.

The physical gesture module 102 of the system 100 may perform functionality, steps, operations, commands and/or instructions as illustrated in one or more of FIGS. 2A, 2B, 2C, 2D, 2E, 3 and 4, ("FIGS. 2A-4").

The device pose module 104 of the system 100 may perform functionality, steps, operations, commands and/or instructions as illustrated in one or more of FIGS. 2A-4.

The tracking module 106 of the system 100 may perform functionality, steps, operations, commands and/or instructions as illustrated in one or more of FIGS. 2A-4.

The augmented reality module 108 of the system 100 may perform functionality, steps, operations, commands and/or instructions as illustrated in one or more of FIGS. 2A-4.

The 3D object rendering module 110 of the system 100 may perform functionality, steps, operations, commands and/or instructions as illustrated in one or more of FIGS. 2A-4.

The virtual interaction module 112 of the system 100 may perform functionality, steps, operations, commands and/or instructions as illustrated in one or more of FIGS. 2A-4.

The user interface module 114 of the system 100 may perform functionality, steps, operations, commands and/or instructions as illustrated in one or more of FIGS. 2A-4.

A database 120 associated with the system 100 maintains information, such as 3D medical model data 124, in a manner the promotes retrieval and storage efficiency and/or data security. In addition, the model data 124 may include rendering parameters, such as data based on selections and modifications to a 3D virtual representation of a medical model rendered for a previous Augmented Reality (AR) display. In various embodiments, one or more rendering parameters may be preloaded as a default value for a rendering parameter in a newly initiated session of the interaction module 112.

In various embodiments, the interaction module 112 accesses one or more storage locations that contain respective portions of medical model data 124. The medical model data 124 may be represented according to two-dimensional (2D) and three-dimensional (3D) medical model data. The 2D and/or 3D ("2D/3D") medical model data 124 may include a plurality of slice layers of medical data associated with external and internal anatomies. For example, the 2D/3D medical model data 124 may include a plurality of slice layers of medical data for generating renderings of external and internal anatomical regions of a user's head, brain and skull. It is understood that various embodiments may be directed to generating displays of any internal or external anatomical portions of the human body and/or animal bodies.

The interaction module 112 may render the 3D virtual medical model in an AR display based on the 3D medical model data. In addition, the interaction module 112 renders the 3D virtual medical model based on model pose data which describes an orientation and position of the rendering of the 3D virtual medical model. The interaction module 112 applies the model pose data to the 3D medical model data to determine one or more positional coordinates in the unified 3D coordinate system for portion(s) of model data of a slice layer(s) that represent various anatomical locations.

The interaction module 112 further renders the 3D virtual medical model based on a current device pose of an AR headset device worn by the user. The current device pose represents a current position and orientation of the AR headset device in the physical world. The interaction module 112 translates the current device pose to a position and orientation within the unified 3D coordinate system to determine the user's perspective view of the AR display. The interaction module 112 generates a rendering of the 3D virtual medical model according to the model pose data for display to the user in the AR display according to the user's perspective view. Similarly, the interaction module 112 generates instrument pose data based on a current pose of a physical instrument. The current instrument pose represents a current position and orientation of a physical instrument in the physical world. For example, the physical instrument may be held by a user's hands and may have one or more fiducial markers. The interaction module 112 translates the current instrument pose to a position and orientation within the unified 3D coordinate system to determine the physical instrument's display position and orientation in the AR display and/or placement with respect to one or more virtual objects. It is understood that the interaction module 112 continually updates the instrument pose data to represent subsequent changes in the position and orientation of the physical instrument.

Various embodiments described herein provide functionality for selection of menu functionalities and positional display coordinates. For example, the interaction module 112 tracks one or more physical gestures such as movement of a user's hand(s) and/or movement of a physical instrument(s) via one or more tracking algorithms to determine directional data to further be utilized in determining whether one or more performed physical gestures indicate a selection of one or more types of functionalities accessible via the AR display and/or selection and execution of a virtual interaction(s). For example, the interaction module 112 may track movement of the user's hand that results in movement of a physical instrument and/or one or more virtual offsets and virtual objects associated with the physical instrument. The interaction module 112 may determine respective positions and changing positions of one or more hand joints or one or more portions of the physical instrument. In various embodiments, the interaction module 112 may implement a simultaneous localization and mapping (SLAM) algorithm.

The interaction module 112 may generate directional data based at least in part on average distances between the user's palm and the user's fingers and/or hand joints or distances between portions (physical portions and/or virtual portions) of a physical instrument. In some embodiments, the interaction module 112 generates directional data based on detected directional movement of the AR headset device worn by the user. The interaction module 112 determines that the directional data is based on a position and orientation of the user's hand(s) (or the physical instrument) that indicates a portion(s) of a 3D virtual object with which the user seeks to select and/or virtually interact with and/or manipulate.

According to various embodiments, the interaction module 112 may implement a collision algorithm to determine a portion of a virtual object the user seeks to select and/or virtually interact with. For example, the interaction module 112 may track the user's hands and/or the physical instrument according to respective positional coordinates in the unified 3D coordinate system that correspond to the orientation of the user's hands and/or the physical instrument in the physical world. The interaction module 112 may detect that one or more tracked positional coordinates may overlap (or be the same as) one or more positional coordinates for displaying a particular portion(s) of a virtual object. In response to detecting the overlap (or intersection), the interaction module 112 determines that the user seeks to select and/or virtually interact with the portion(s) of the particular virtual object displayed at the overlapping positional coordinates.

According to various embodiments, upon determining the user seeks to select and/or virtually interact with a virtual object, the interaction module 112 may detect one or more changes in hand joint positions and/or physical instrument positions and identify the occurrence of the position changes as a performed selection function. For example, a performed selection function may represent an input command to the interaction module 112 confirming the user is selecting a portion of a virtual object via a ray casting algorithm and/or collision algorithm. For example, the performed selection function may also represent an input command to the interaction module 112 confirming the user is selecting a particular type of virtual interaction functionality. For example, the user may perform a physical gesture of tips of two fingers touching to correspond to a virtual interaction representing an input command, such as a select input command.

The interaction module 112 identifies one or more virtual interactions associated with the detected physical gestures. In various embodiments, the interaction module 112 identifies a virtual interaction selected by the user, or to be performed by the user, based on selection of one or more functionalities from a 3D virtual menu displayed in the AR display. In addition, the interaction module 112 identifies a virtual interaction selected by the user according to one or more pre-defined gestures that represent input commands for the interaction module 112. In some embodiments, a particular virtual interaction may be identified based on a sequence of performed physical gestures detected by the interaction module 112. In some embodiments, a particular virtual interaction may be identified as being selected by the user based on a series of preceding virtual interactions.

Figure 2A:
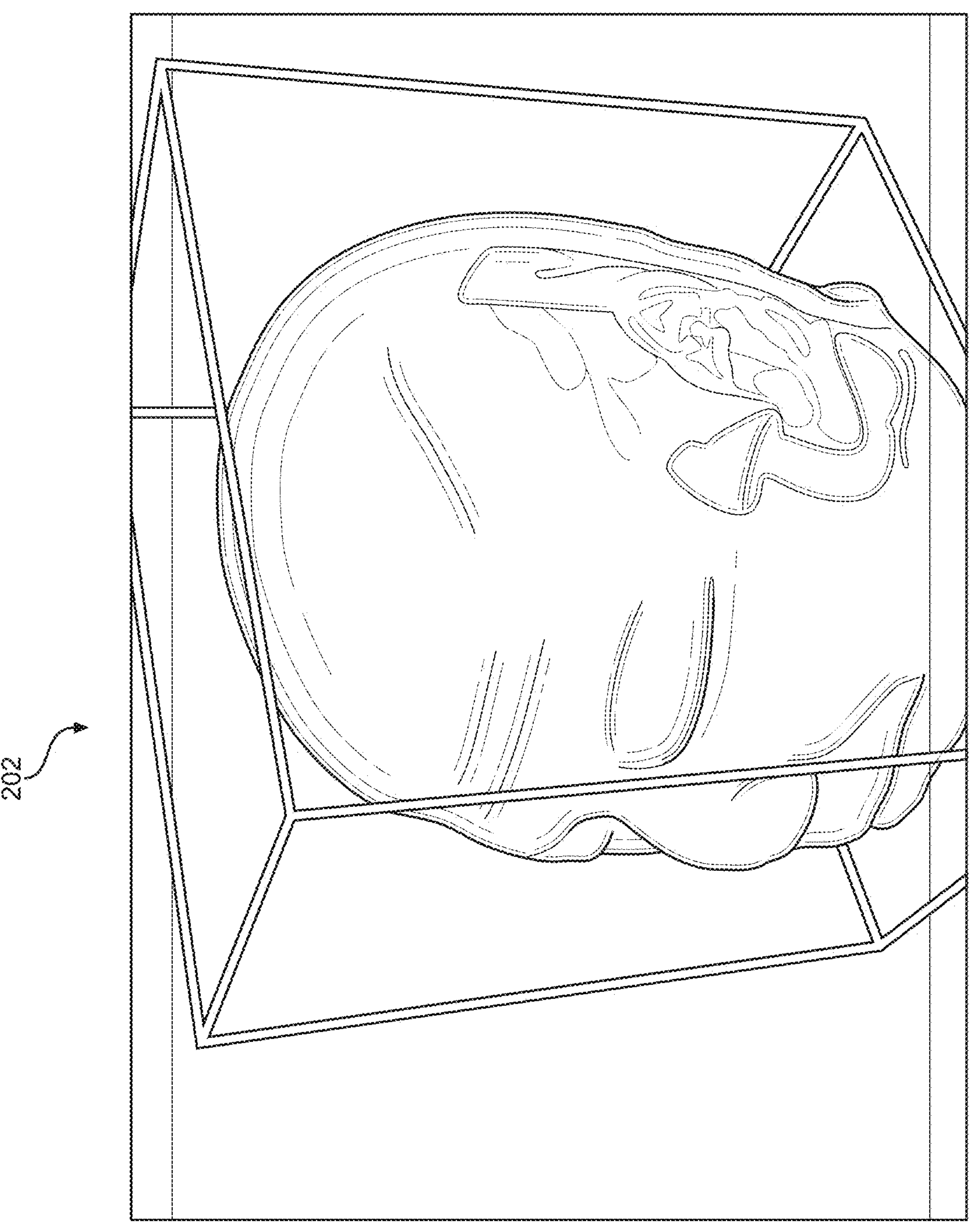
FIG. 2A illustrates a head scan of a patient performed by a DTI processing procedure according to example embodiments.

FIG. 2A illustrates a head scan of a patient performed by a diffusion tensor imaging (DTI) processing procedure according to example embodiments. Referring to FIG. 2A, the DTI scan 202 may be performed to a patient's head area or other areas depending on a desired result by the medical personnel. According to example embodiments a patient's head may be scanned by a scanning technology, such as a magnetic resonance imaging (MRI), a computed tomography (CT) scan, and a diffusion tensor imaging (DTI). Specifically, the DTI scan is a noninvasive MRI technique that uses the movement of water molecules to create images that visualize neural pathways and connectivity in the brain. DTI scans can be used to study the white matter architecture of the brain, and can be used to identify abnormalities, such as a brain tumor.

Figure 2B:
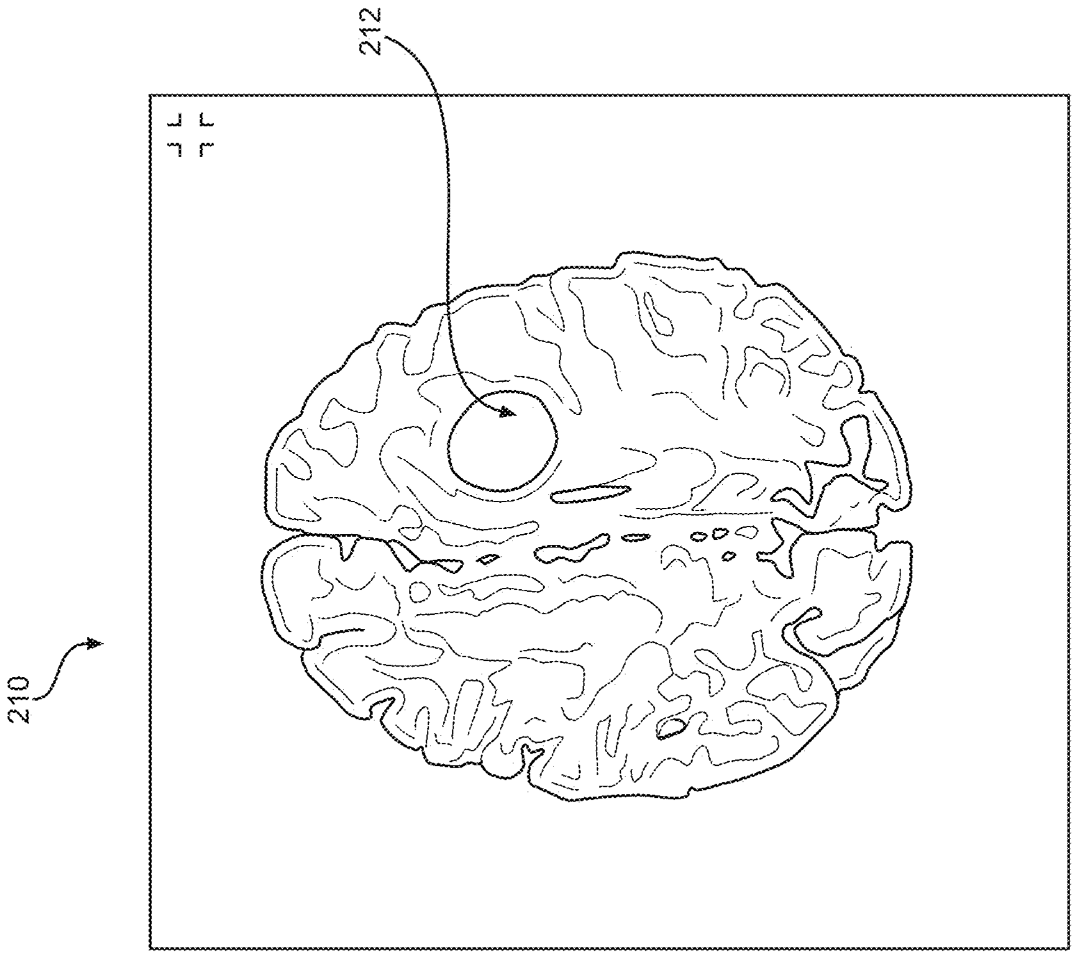
FIG. 2B illustrates a portion of a head scan of a patient performed by a DTI processing procedure revealing a brain abnormality according to example embodiments.

FIG. 2B illustrates a portion of a head scan of a patient performed by a DTI processing procedure revealing a brain abnormality according to example embodiments. Referring to FIG. 2B, the particular image slice example 210 illustrates an area of the brain where a brain abnormality exists, such as a brain tumor 212.

Figure 2C:
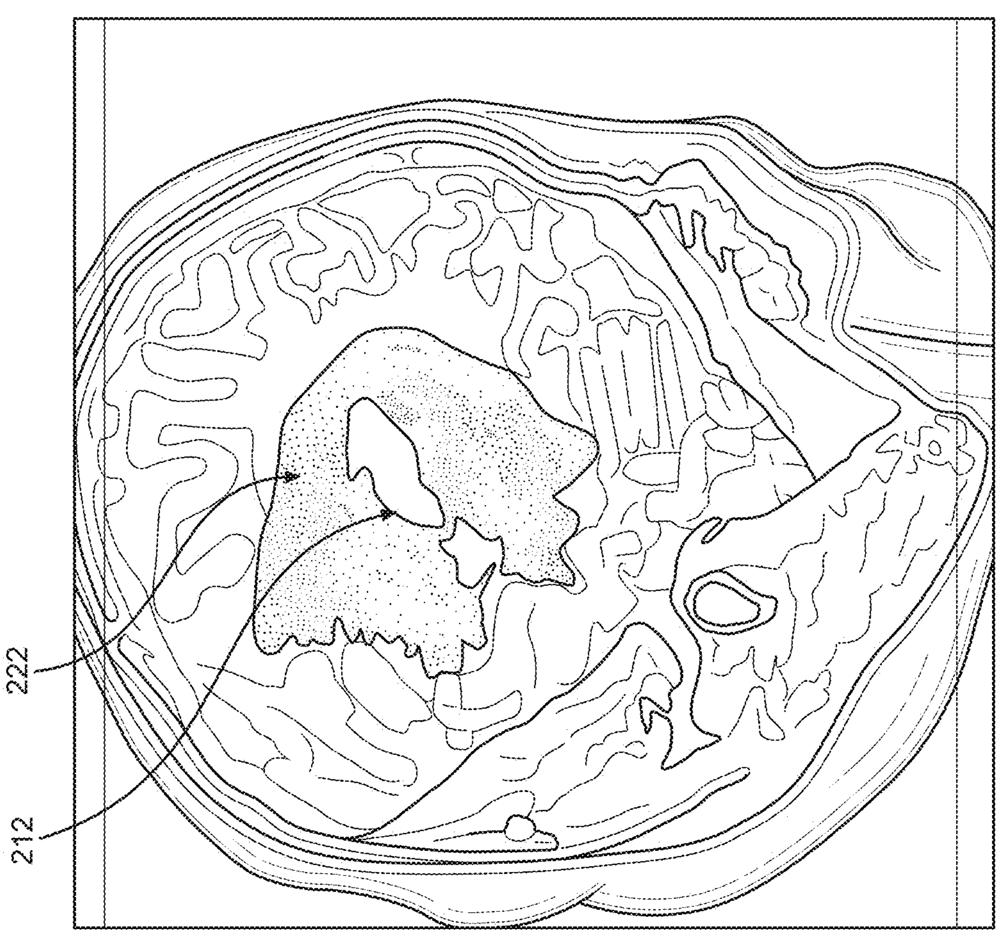
FIG. 2C illustrates a merged head scan of a patient illustrating a region of interest (ROI) according to example embodiments.
Figure 2D:
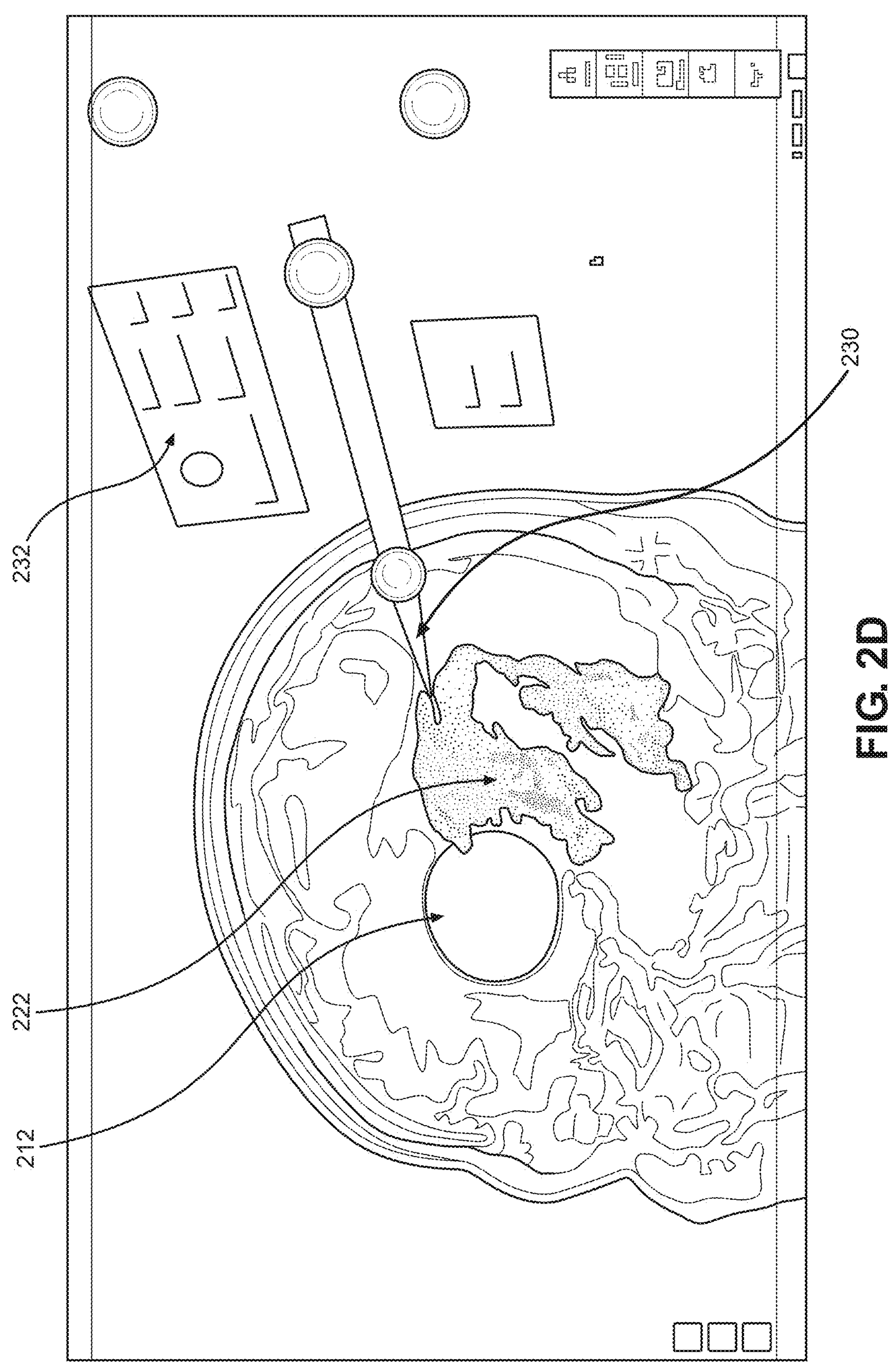
FIG. 2D illustrates a merged head scan of a patient illustrating a region of interest (ROI) as selected by a virtual selection instrument according to example embodiments.

FIG. 2C illustrates a merged head scan of a patient illustrating a region of interest (ROI) according to example embodiments. Referring to FIG. 2C, a region of interest 212 may be referred to as a fiber bundle of brain tissue 222 which is selected by a user/doctor attempting to isolate an area of the brain near the abnormality. The ROI may be used as a basis for an area that is being identified that is near the abnormality and which should be considered prior to any surgery or other procedure. The highlighted ROI 222 can be illuminated by the medical imaging display and the other areas can remain darker or gray until selected by a AR selection procedure.

The DTI scan is a sub-type of MRI that can be used to identify fiber bundles in the brain, such as a particular set of bundles which can be customized to define a region of interest (ROI). The ROI may be established to include a colorized and/or highlighted portion of the original MRI image that is adjacent or contiguous to an abnormality, such as a tumor. The fiber bundle may be defined as a set of anatomical connections between brain cells. In the event that a tumor is present somewhere in the brain area defined by the MRI, the fiber bundle 222 that is near and/or which surrounds that particular area can be identified as the fiber bundle around the tumor region or simply the ROI.

FIG. 2C illustrates a merged head scan of a patient illustrating a region of interest (ROI) according to example embodiments. Referring to FIG. 2C, a hand-held instrument or other AR selection procedure can be used to introduce a virtual selection instrument 230 that invokes a highlighted area when a selection is made. The information and control functions may be displayed 232 as a menu in the display used to realize the merged scan information.

Using the hand-held instrument 230 or other type of instrument, a user, such as a doctor or technician, can selectively identify and import part of the fiber bundles 222 of an image of a brain to display the fiber bundles on a rendered 3-D model. The instrument may be used by bringing a tip of instrument near an actual person's head or other body part. A virtual extension of the instrument, such as a virtual elongated pointer portion may appear in a visualization space on a monitor of a device, and/or a headset worn by a user. The virtual representation of the instrument provides a way to select parts of a human's anatomy without actually entering the person's body. In turn, this permits a user to select a coordinate location of a ROI over a physical patient laying in the operating room or in a similar environment. In some embodiments, the ROI may be an ROI modeled according to tractography.

Once an area is selected for rendering in a combined image set including the DTI scan and/or a combination of the DTI scan and the 3-D medical model, the data around the intersection point may be rendered to identify the ROI with the fiber bundle portion of a patient brain as colorized and/or highlighted while the remaining portions remain gray and darker (non-colorized).

Figure 2E:
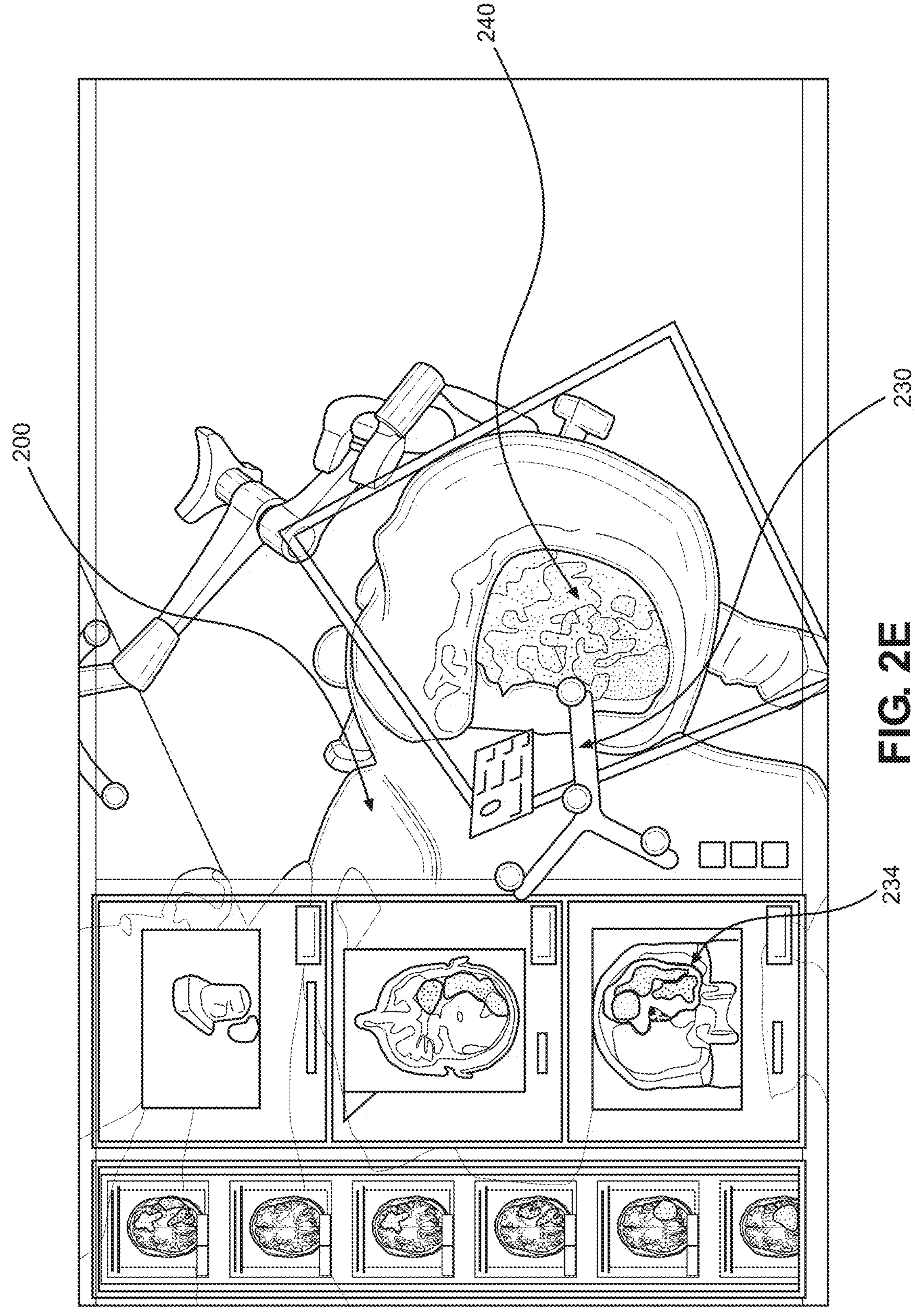
FIG. 2E illustrates a merged head scan of a patient displayed while a live patient is being examined by the virtual selection instrument according to example embodiments.

FIG. 2E illustrates a merged head scan of a patient displayed while a live patient is being examined by the virtual selection instrument according to example embodiments. Referring to FIG. 2E, the display demonstrates a live patient 200 being examined and having a planar space identified by the instrument 230 to include a virtual slice 240 of the brain tissue illustrated when the instrument is brought into virtual contact with the patient body. The colorization and highlighted portions may be displayed in real-time to provide additional confirmation of the patient's anatomical brain structure. The display may also include certain 2-D images 234 demonstrating other angles and ROI.

Once the rendering is completed by a computing processing module, the displayed image data may be manipulated by using the hand-held instrument or via other rotating and selection operations (e.g., head movement, hand movements, dragging/pinching operations, etc.). Ideally, the fiber bundle will stay in the same coordinated based planar location while any rotational perspectives are performed.

In order to select a ROI. The instrument's virtual tip may virtually touch a specific fiber bundle(s) 222 and a selection can be made by a button selection or other selection operation performed by a user. A fiber bundle 222 may include a contorted area of the brain as identified from the scan, such as for example a certain number of lines, then the other areas of the brain can be faded out to a darker grayscale. The selected fibers may be highlighted at a virtual intersection that crosses an area of the virtual instrument tip. The ROI may be analyzed from the DTI scan. However, the MRI scan can provide a comprehensive view of the entire head. In some embodiments, the ROI may be an ROI modeled according to tractography.

A registration operation may be performed to combine the DTI data scan with a basic MRI scan or other 3D anatomical model. The process for registration includes a mutual information computation. Computing the mutual information may include iterative comparison operations which compare data from one 3-D space of the DTI scan data to another 3-D space, such as an anatomical model or a different type of MRI scan (e.g., base MRI scan, CT scan, etc.). During the special analysis of the mutual information processing, the process may include identifying similarities by comparison based on pixel data intensities of both scans. The similar pixel intensities may be paired for a particular location in the 3-D space. This approach enables fiber bundles to be selected and displayed for one particular area of a patient's head. As a result, highlighting the bands associated with the ROI by using the virtual instrument tip, may offer a way to selectively highlight a portion of the 3-D image of a user's brain. When the virtual instrument tip selects a set of fibers in a 3-D image scan, the virtually intersected portions are highlighted with illumination and/or color on a display and the other portions of the image are maintained at a different color or illumination level.

Once a ROI is selected, when the instrument is brought to a live person, the scan may be registered with the live patient which permits the instrument to be used on the person to invoke a display rendering on the display while the instrument is brought within a virtual location of the person. The registration is performed by reiterative processing of the mutual information between the DTI scan and the base scan (e.g., regular MRI, CT scan. etc.). In operation, when the registration is competed, and the instrument is next to the actual patient, the selectively rendering provides an image of anything that is close to the tip or virtual tip as it appears inside the virtual head. In general, the different colors represent different regions of the brain, however, colors can be assigned by the user. A user can selectively render different regions of ROI and different region of the fiber bundle. Applying coloring to the grayscale image assists with viewing separate regions of the brain.

Figure 3:
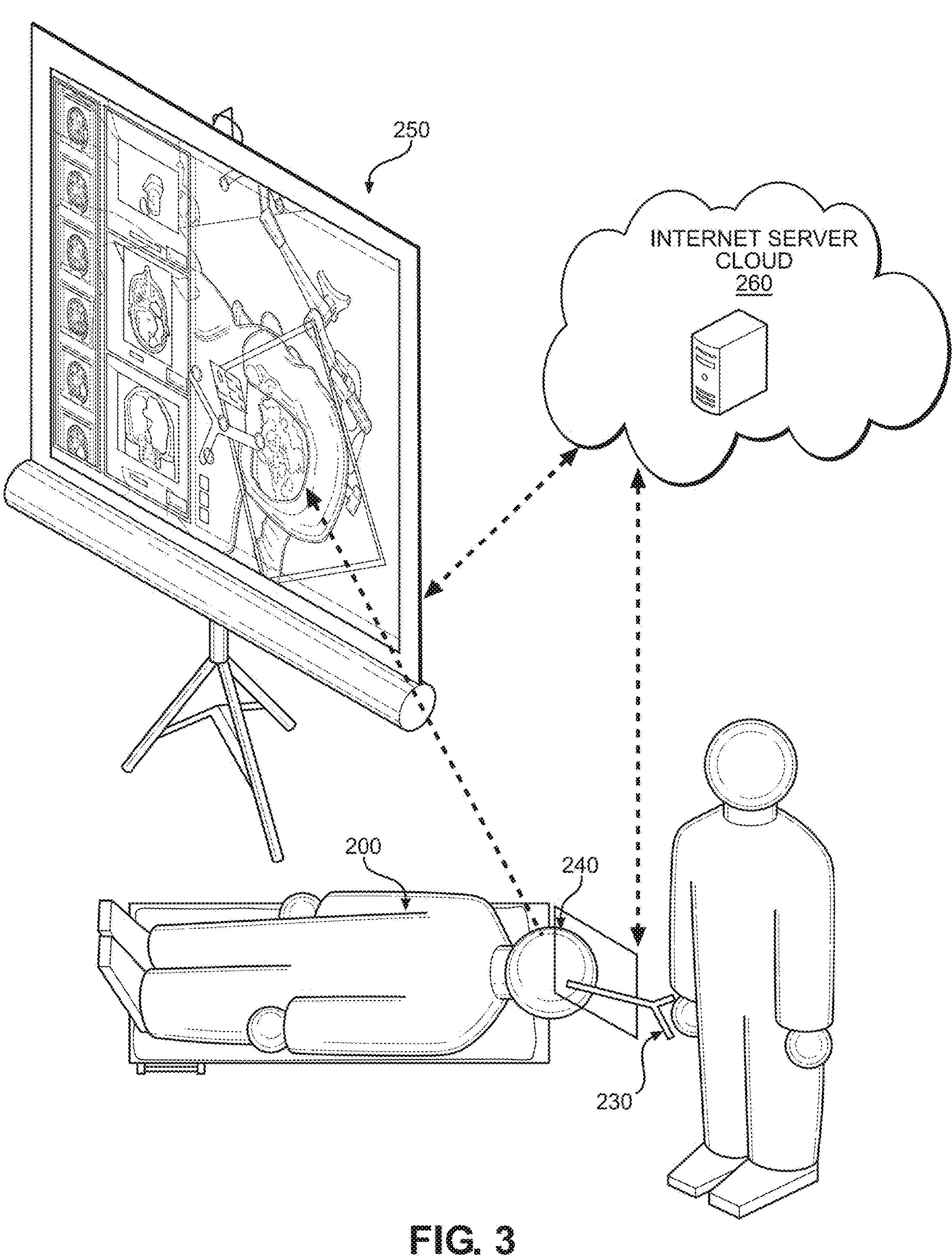
FIG. 3 illustrates network configuration of a live patient being examined according to example embodiments.

FIG. 3 illustrates network configuration of a live patient being examined according to example embodiments. Referring to FIG. 3, once the merged scan data is saved and any ROI is identified and rendered. The merged scan data may be available for examination purposes. In an operating room (OR), the doctor may use an instrument 230 to explore a virtual representation of the patient brain by selecting a positional plane 240 of the patient head, which can be illustrated in real-time on a nearby display 250 via processing of information stored in a local or remote server 260.

Figure 4:
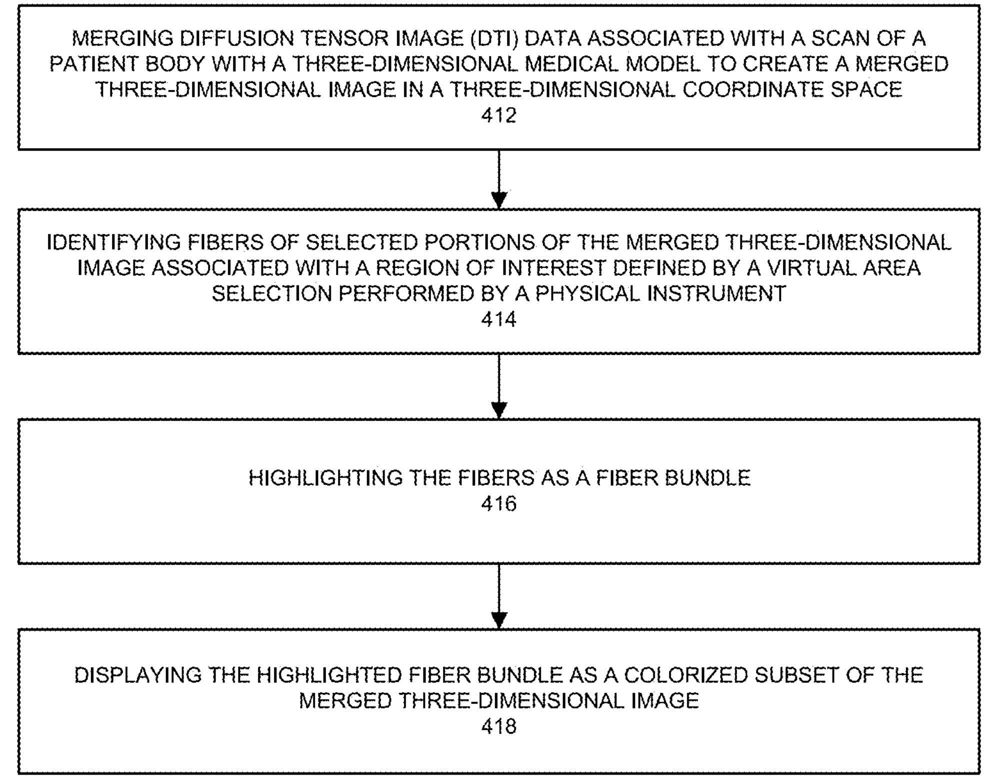
FIG. 4 illustrates an example process according to example embodiments.

FIG. 4 illustrates an example process according to example embodiments. Referring to FIG. 4, the process may include merging diffusion tensor image (DTI) data associated with a scan of a patient body with a three-dimensional medical model to create a merged three-dimensional image in a three-dimensional coordinate space 412, identifying fibers of selected portions of the merged three-dimensional image associated with a region of interest defined by a virtual area selection performed by a physical instrument 414, highlighting the fibers as a fiber bundle 416, and displaying the highlighted fiber bundle as a colorized subset of the merged three-dimensional image 418.

The process may also include displaying areas other than the fiber bundle of the three-dimensional image as a grayscale color, applying a plurality of different colors to the merged three-dimensional image as respective different regions of a brain of the scan of the patient body, and displaying the merged three-dimensional image including the brain with the highlighted fiber bundle and the plurality of different colors. The identifying the fibers and the region of interest are selected by a virtual portion of the physical instrument making contact with the region of interest inside the merged three-dimensional image. The three-dimensional medical model may be a magnetic resonance imaging (MRI) scan. The merging the (DTI) data associated with a three-dimensional medical model may include matching intensities one or more pixelated portions of the DTI data with intensities one or more pixelated portions of the three-dimensional medical model.

Although an exemplary embodiment of at least one of a system, method, and non-transitory computer readable media has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

Figure 5:
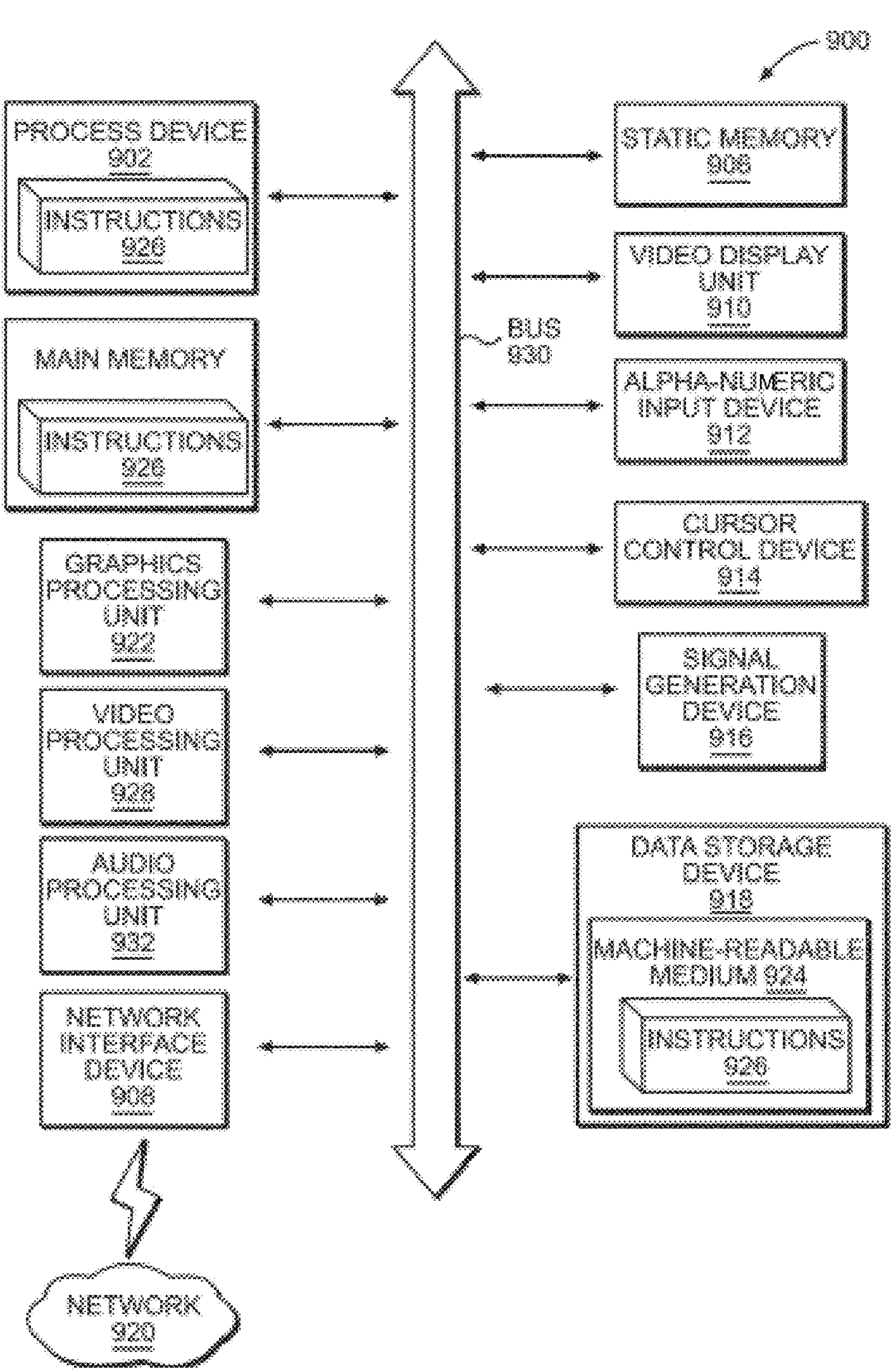
FIG. 5 illustrates an example computing platform used to perform one or more operations associated with example embodiments.

FIG. 5 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 900 includes a processing device 902, a main memory 904 (e.g., read-only memory (ROM), flash memory, dynamic random access memory (DRAM) such as synchronous DRAM (SDRAM) or Rambus DRAM (RDRAM), etc.), a static memory 906 (e.g., flash memory, static random access memory (SRAM), etc.), and a data storage device 918, which communicate with each other via a bus 930.

Processing device 902 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. The processing device 902 is configured to execute instructions 926 for performing the operations and steps discussed herein.

The computer system 900 may further include a network interface device 908 to communicate over the network 920. The computer system 900 also may include a video display unit 910 (e.g., a liquid crystal display (LCD) or a cathode ray tube (CRT)), an alphanumeric input device 912 (e.g., a keyboard), a cursor control device 914 (e.g., a mouse), a graphics processing unit 922, a signal generation device 916 (e.g., a speaker), graphics processing unit 922, video processing unit 928, and audio processing unit 932.

The data storage device 918 may include a machine-readable storage medium 924 (also known as a computer-readable medium) on which is stored one or more sets of instructions or software 926 embodying any one or more of the methodologies or functions described herein. The instructions 926 may also reside, completely or at least partially, within the main memory 904 and/or within the processing device 902 during execution thereof by the computer system 900, the main memory 904 and the processing device 902 also constituting machine-readable storage media.

In one implementation, the instructions 926 include instructions to implement functionality corresponding to the components of a device to perform the disclosure herein. While the machine-readable storage medium 924 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMS, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A method comprising:

merging diffusion tensor image (DTI) data associated with a scan of a patient body with a three-dimensional medical model to create a merged three-dimensional image in a three-dimensional coordinate space;

identifying fibers of selected portions of the merged three-dimensional image associated with a region of interest defined by a virtual area selection performed by a physical instrument;

highlighting the fibers as a fiber bundle; and displaying the highlighted fiber bundle as a colorized subset of the merged three-dimensional image, wherein the identified fibers and the region of interest are selected by a virtual portion of the physical instrument making contact with the region of interest inside the merged three-dimensional image.

2. The method of claim 1, further comprising displaying areas other than the fiber bundle of the three-dimensional image as a grayscale color.

3. The method of claim 1, further comprising applying a plurality of different colors to the merged three-dimensional image as respective different regions of a brain of the scan of the patient body; and displaying the merged three-dimensional image including the brain with the highlighted fiber bundle and the plurality of different colors.

4. The method of claim 1, wherein the three-dimensional medical model comprises a magnetic resonance imaging (MRI) scan.

5. The method of claim 1, wherein the merging the (DTI) data associated with a three-dimensional medical model comprises matching intensities one or more pixelated portions of the DTI data with intensities one or more pixelated portions of the three-dimensional medical model.

6. The method of claim 1, further comprising:

accessing one or more storage locations containing portions of medical model data, the medical model data comprising a plurality of slice layers of medical data associated with external or internal anatomies; and rendering displays of the external or internal anatomies using the plurality of the slice layers.

7. The method of claim 1, further comprising:

rendering the three-dimensional medical model in an augmented reality display, based on data from the three-dimensional medical model.

8. The method of claim 1, further comprising:

rendering the three-dimensional medical model, based on a model pose data, the model pose data, describing an orientation and position of the rendering; and applying the model pose data to the three-dimensional medical model; and determining one or more positional coordinates in the three-dimensional coordinate space for portions of a model of a plurality of slice layers, representing anatomical locations.

9. The method of claim 1, further comprising:

rendering a virtual medical model, based on a current device pose of an augmented reality headset device worn by a user.

10. The method of claim 1, further comprising:

rendering the three-dimensional medical model in an augmented reality display;

rendering the three-dimensional medical model, based on a current device pose of an augmented reality headset device worn by a user, the current device pose representing a current position and orientation of the augmented reality headset device in the physical world; and translating the current device pose to a position and orientation within the three-dimensional coordinate space;

generating a user perspective view of the augmented reality display; and displaying the user perspective view of the augmented reality display.

11. A system comprising one or more processors, and a non-transitory computer-readable medium including one or more sequences of instructions that, when executed by the one or more processors, cause the system to perform operations comprising:

merging diffusion tensor image (DTI) data associated with a scan of a patient body with a three-dimensional medical model to create a merged three-dimensional image in a three-dimensional coordinate space;

identifying fibers of selected portions of the merged three-dimensional image associated with a region of interest defined by a virtual area selection performed by a physical instrument;

highlighting the fibers as a fiber bundle; and displaying the highlighted fiber bundle as a colorized subset of the merged three-dimensional image, wherein the identified fibers and the region of interest are selected by a virtual portion of the physical instrument making contact with the region of interest inside the merged three-dimensional image.

12. The system of claim 11, wherein the one or more sequences of instructions, when executed by the one or more processors, cause the system to further perform:

displaying areas other than the fiber bundle of the three-dimensional image as a grayscale color.

13. The system of claim 11, wherein the one or more sequences of instructions, when executed by the one or more processors, cause the system to further perform:

applying a plurality of different colors to the merged three-dimensional image as respective different regions of a brain of the scan of the patient body; and displaying the merged three-dimensional image including the brain with the highlighted fiber bundle and the plurality of different colors.

14. The system of claim 11, wherein the three-dimensional medical model comprises a magnetic resonance imaging (MRI) scan.

15. The system of claim 11, wherein the merging the (DTI) data associated with a three-dimensional medical model comprises matching intensities one or more pixelated portions of the DTI data with intensities one or more pixelated portions of the three-dimensional medical model.

16. A non-transitory computer-readable medium having a computer-readable program code embodied therein to be executed by one or more processors, the program code including instructions to perform:

merging diffusion tensor image (DTI) data associated with a scan of a patient body with a three-dimensional medical model to create a merged three-dimensional image in a three-dimensional coordinate space;

identifying fibers of selected portions of the merged three-dimensional image associated with a region of interest defined by a virtual area selection performed by a physical instrument;

highlighting the fibers as a fiber bundle; and displaying the highlighted fiber bundle as a colorized subset of the merged three-dimensional image, wherein the identified fibers and the region of interest are selected by a virtual portion of the physical instrument making contact with the region of interest inside the merged three-dimensional image.

17. The non-transitory computer-readable medium of claim 16, wherein the program code includes instructions to further perform:

displaying areas other than the fiber bundle of the three-dimensional image as a grayscale color.

18. The non-transitory computer-readable medium of claim 16, wherein the program code includes instructions to further perform:

applying a plurality of different colors to the merged three-dimensional image as respective different regions of a brain of the scan of the patient body; and displaying the merged three-dimensional image including the brain with the highlighted fiber bundle and the plurality of different colors.

19. The non-transitory computer-readable medium of claim 16, wherein the three-dimensional medical model comprises a magnetic resonance imaging (MRI) scan.

20. The non-transitory computer-readable medium of claim 16, wherein the merging the (DTI) data associated with a three-dimensional medical model comprises matching intensities one or more pixelated portions of the DTI data with intensities one or more pixelated portions of the three-dimensional medical model.

* * * * *